(12) United States Patent
Fell

(10) Patent No.: US 7,819,919 B2
(45) Date of Patent: Oct. 26, 2010

(54) SURGICALLY IMPLANTABLE KNEE PROSTHESIS

(76) Inventor: Barry M. Fell, 7124 Red Top Rd., Hummelstown, PA (US) 17036

( * ) Notice: Subject to any disclaimer, the term of this patent is extended or adjusted under 35 U.S.C. 154(b) by 102 days.

(21) Appl. No.: 11/940,606

(22) Filed: Nov. 15, 2007

(65) Prior Publication Data

US 2009/0118830 A1 May 7, 2009

Related U.S. Application Data

(63) Continuation-in-part of application No. 10/831,872, filed on Apr. 26, 2004, now Pat. No. 7,297,161.

(51) Int. Cl.
*A61F 2/38* (2006.01)
(52) U.S. Cl. .............. 623/14.12; 623/20.29; 623/20.3
(58) Field of Classification Search .............. None
See application file for complete search history.

(56) References Cited

U.S. PATENT DOCUMENTS

| | | |
|---|---|---|
| 3,869,731 A | 3/1975 | Waugh et al. |
| 4,085,466 A | 4/1978 | Goodfellow et al. |
| 4,207,627 A | 6/1980 | Cloutier |
| 4,224,696 A | 9/1980 | Murray et al. |
| 4,257,129 A | 3/1981 | Volz |
| 4,340,978 A | 7/1982 | Buechel et al. |
| 4,344,193 A | 8/1982 | Kenny |
| 4,385,404 A | 5/1983 | Sully et al. |
| 4,446,578 A | 5/1984 | Perkins et al. |
| 4,502,161 A | 3/1985 | Wall |
| 4,759,767 A | 7/1988 | Lacey |
| 4,808,185 A | 2/1989 | Penenberg et al. |
| 4,822,362 A | 4/1989 | Walker et al. |
| 4,865,607 A | 9/1989 | Witzel et al. |
| 4,883,488 A | 11/1989 | Bloebaum et al. |
| 4,919,667 A | 4/1990 | Richmond |
| 4,936,853 A | 6/1990 | Fabian et al. |
| 5,007,934 A | 4/1991 | Stone |
| 5,067,964 A | 11/1991 | Richmond et al. |
| 5,137,536 A | 8/1992 | Koshino |

(Continued)

FOREIGN PATENT DOCUMENTS

DE 3840470 6/1990

(Continued)

OTHER PUBLICATIONS

Wheeler, John, "Little Device Could Pack a Big Punch," Sulzer Medica Journal Feb. 2000, pp. 16-17.

(Continued)

*Primary Examiner*—David H Willse
*Assistant Examiner*—Javier G Blanco
(74) *Attorney, Agent, or Firm*—Brooks Kushman P.C.

(57) ABSTRACT

A prosthesis is provided for implantation into a knee joint compartment between a femoral condyle and its corresponding tibial plateau without requiring bone resection. The prosthesis includes a body having a generally elliptical shape in plan and a pair of opposed surfaces where one of the surfaces is generally concave. The body further includes an exterior portion and an interior portion, where the exterior portion is constructed from a higher modulus material than the interior portion such that the body is at least slightly deformable.

24 Claims, 5 Drawing Sheets

U.S. PATENT DOCUMENTS

| | | | |
|---|---|---|---|
| 5,171,283 A | 12/1992 | Pappas et al. |
| 5,171,322 A | 12/1992 | Kenny |
| 5,176,710 A | 1/1993 | Hahn et al. |
| 5,271,737 A | 12/1993 | Baldwin et al. |
| 5,282,868 A | 2/1994 | Bahler |
| 5,336,266 A | 8/1994 | Caspari et al. |
| 5,344,459 A | 9/1994 | Swartz |
| 5,358,530 A | 10/1994 | Hodorek |
| 5,358,531 A | 10/1994 | Goodfellow et al. |
| 5,387,240 A | 2/1995 | Pottenger et al. |
| 5,395,376 A | 3/1995 | Caspari et al. |
| 5,395,401 A | 3/1995 | Bahler |
| 5,405,396 A | 4/1995 | Heldreth et al. |
| 5,658,342 A | 8/1997 | Draganich et al. |
| 5,683,468 A | 11/1997 | Pappas |
| 5,702,466 A | 12/1997 | Pappas et al. |
| 5,725,584 A | 3/1998 | Walker et al. |
| 5,776,200 A | 7/1998 | Johnson et al. |
| 5,782,925 A | 7/1998 | Collazo et al. |
| 5,871,541 A | 2/1999 | Gerber |
| 5,871,542 A | 2/1999 | Goodfellow et al. |
| 5,871,543 A | 2/1999 | Hofmann |
| 5,871,545 A | 2/1999 | Goodfellow et al. |
| 5,879,394 A | 3/1999 | Ashby et al. |
| 5,957,979 A | 9/1999 | Beckman et al. |
| 5,964,808 A | 10/1999 | Blaha et al. |
| 6,013,103 A | 1/2000 | Kaufman et al. |
| 6,090,144 A | 7/2000 | Letot et al. |
| 6,123,728 A | 9/2000 | Brosnahan et al. |
| 6,165,223 A | 12/2000 | Metzger et al. |
| 6,206,927 B1 | 3/2001 | Fell et al. |
| 6,210,444 B1 | 4/2001 | Webster et al. |
| 6,245,110 B1 | 6/2001 | Grundei et al. |
| 6,258,126 B1 | 7/2001 | Colleran |
| 6,258,127 B1 | 7/2001 | Schmotzer |
| 6,299,645 B1 | 10/2001 | Ogden |
| 6,413,279 B1 | 7/2002 | Metzger et al. |
| 6,428,577 B1 | 8/2002 | Evans et al. |
| 6,558,421 B1 | 5/2003 | Fell et al. |
| 6,629,997 B2 | 10/2003 | Mansmann |
| 6,660,039 B1 | 12/2003 | Evans et al. |
| 6,679,914 B1 | 1/2004 | Gabbay |
| 6,726,724 B2 | 4/2004 | Repicci |
| 6,855,165 B2 | 2/2005 | Fell et al. |
| 6,866,684 B2 | 3/2005 | Fell et al. |
| 6,875,235 B2 | 4/2005 | Ferree |
| 6,893,463 B2 | 5/2005 | Fell et al. |
| 6,911,044 B2 | 6/2005 | Fell et al. |
| 6,923,831 B2 | 8/2005 | Fell et al. |
| 2002/0173855 A1 | 11/2002 | Mansmann |
| 2003/0060884 A1 | 3/2003 | Fell et al. |
| 2003/0060888 A1 | 3/2003 | Fell et al. |
| 2004/0006393 A1 | 1/2004 | Burkinshaw |
| 2004/0006394 A1 | 1/2004 | Lipman et al. |
| 2004/0133275 A1 | 7/2004 | Mansmann |
| 2004/0153163 A1 | 8/2004 | Posner |
| 2004/0199250 A1 | 10/2004 | Fell |
| 2004/0220677 A1 | 11/2004 | Delfosse et al. |
| 2004/0267363 A1 | 12/2004 | Fell et al. |
| 2005/0033424 A1 | 2/2005 | Fell |
| 2005/0171604 A1 | 8/2005 | Michalow |
| 2005/0209703 A1 | 9/2005 | Fell |

FOREIGN PATENT DOCUMENTS

| | | |
|---|---|---|
| EP | 0372811 A1 | 6/1990 |
| EP | 0507645 A1 | 10/1992 |
| EP | 1 095 638 A2 | 2/2001 |
| FR | 2635678 | 3/1990 |
| FR | 2700263 | 7/1994 |
| FR | 2747914 | 10/1997 |
| GB | 2278782 A | 12/1994 |
| GB | 2302282 A | 1/1997 |
| GB | 2312166 A | 10/1997 |
| WO | WO 9426204 A1 | 11/1994 |
| WO | WO 95/27450 | 10/1995 |

OTHER PUBLICATIONS

Supplementary European Search Report for the corresponding EP Patent Application 05736167.7 mailed Dec. 15, 2009.

SURGICALLY IMPLANTABLE KNEE PROSTHESIS

CROSS-REFERENCE TO RELATED APPLICATIONS

This application is a continuation-in-part of U.S. application Ser. No. 10/831,872 filed Apr. 26, 2004, now U.S. Pat. No. 7,297,161.

BACKGROUND OF THE INVENTION

1. Field of the Invention

The present invention pertains to a prosthetic device which is surgically implantable into a body joint, and more particularly to a knee joint prosthesis which may be surgically implanted between the femoral condyle and tibial plateau of the knee compartment.

2. Background Art

Articular cartilage and meniscal cartilage provide the mobile weight bearing surfaces of the knee joint. Damage to these surfaces is generally due to genetic predisposition, trauma, and/or aging. The result is usually the development of chondromalacia, thinning and softening of the articular cartilage, and degenerative tearing of the meniscal cartilage. Various methods of treatment are available to treat these disease processes. Each option usually has specific indications and is accompanied by a list of benefits and deficiencies that may be compared to other options.

The healthy knee joint has a balanced amount of joint cartilage across the four surfaces of this bicompartmental joint (medial femoral condyle, medial tibial plateau, lateral femoral condyle, and lateral tibial plateau). In patients with osteoarthritis, the degenerative process typically leads to an asymmetric wear pattern that leaves one compartment with significantly less articular cartilage covering the weight bearing areas of the tibia and femur than the other compartment. Most commonly, the medial compartment of the knee joint is affected more often than the lateral compartment.

As the disease progresses, large amounts of articular cartilage are worn away. Due to the asymmetric nature of the erosion, the alignment of the mechanical axis of rotation of the femur relative to the tibia becomes tilted down towards the compartment which is suffering the majority of the erosion. The result is a varus (bow-legged) deformity in the case of a medial compartment disease predominance, or a valgus (knock-kneed) deformity in the case of lateral compartment disease predominance. Factors such as excessive body weight, previous traumatic injury, knee instability, the absence of the meniscus, and genetic predisposition all affect the rate of the disease.

Osteoarthritis is usually defined in stages of Grade I through V, with Grade III revealing significant articular cartilage loss, Grade IV revealing some eburnation of the subchondral bone, and Grade V detailing both significant articular loss and bone loss. The disease manifests itself as periodic to continuous pain that can be quite uncomfortable for the patient. The cause of this pain is subject to many opinions but it is apparent that, as the joint compartment collapses, the collateral ligament on the side of the predominant disease becomes increasingly slack and the tibial and femoral axes move, for example, from a varus to a valgus condition. This increases the stress on the opposing collateral ligament as well as the cruciate ligaments, and shifts the load bearing function of this bicompartmental joint increasingly towards the diseased side. This increasing joint laxity is suspected of causing some of the pain one feels. In addition, as the bearing loads are shifted, the body responds to the increased loading on the diseased compartment with an increased production of bony surface area (osteophytes) in an attempt to reduce the area unit loading. All of this shifting of the knee component geometry causes a misalignment of the mechanical axis of the joint. This misalignment causes an increase in the rate of degenerative change to the diseased joint surfaces, causing an ever-increasing amount of cartilage debris to build up in the joint, and further causing joint inflammation and subsequent pain.

Currently, there is a void in options used to treat the relatively young patient with moderate to severe chondromalacia involving mainly one compartment of the knee. Current treatments include NSAIDS, cortisone injections, hyaluronic acid (HA) injections, and arthroscopic debridement. Some patients cannot tolerate or do not want the risk of potential side effects of NSAIDS. Repeated cortisone injections actually weaken articular cartilage after a long period of time. HA has shown promising results, but is only a short term solution for pain. Arthroscopic debridement alone frequently does not provide long lasting relief of symptoms.

Unfortunately, the lack of long term success of these treatments leads to more invasive treatment methods. Osteochondral allografts and microfracture techniques are indicated for small cartilage defects that are typically the result of trauma. These procedures are not suitable for addressing large areas of degeneration. In addition, osteochondral allografts can only be used to address defects on the femoral condyle, as tibial degeneration cannot be addressed with this technique. High tibial osteotomy (HTO) corrects the varus malalignment between the tibia and the femur but, because it is performed below the joint line, it does not fill the cartilage void or re-tension the medial collateral ligament (MCL). Removing bone and changing the joint line does not complicate the conversion to total knee arthroscopy (TKA). However, an HTO does leave a hard sclerotic region of bone which is difficult to penetrate, making conversion to a total knee replacement (TKR) technically challenging. Unicompartmental and bicompartmental total knee replacements resect significant amounts of bone and, if performed on younger patients, will likely require revision surgery as they age. Revision total knee replacement surgery is usually extensive and results in predictably diminished mechanical life expectancy. Therefore, it is best to delay this type of bone resecting surgery as long as possible.

The only true solution is to rebuild the defective joint by "filling" the joint space with more articular bearing material through a complete resurfacing of the existing femoral condyle and tibial plateau. By replacing the original cartilage to its pre-diseased depth, the joint mechanical axis alignment is restored to its original condition. Unfortunately, these natural articular materials and surgical technology required to accomplish this replacement task do not yet exist.

Currently, replacement of the existing surfaces, with materials other than articular cartilage, is only possible with a total or uni-condylar knee replacement, and these procedures require removal of significant amounts of the underlying bone structure. The alternative method is to fill the joint space with a spacer that replaces the missing articular materials.

Attaching a new bearing surface to the femoral condyle is technically challenging and was first attempted, with limited success, over 40 years ago with the MGH (Massachusetts General Hospital) knee. Like a dental crown, it covered both the femoral condyles with Vitallium (CoCr) and would bear against the existing tibial plateau. Tibial covering devices such as the McKeever, Macintosh, and Townley tibial tray maintained the existing femoral surface as the bearing surface but, like the MGH knee, all required significant bone resection, thus making them less than ideal solutions as well. These devices also made no particular attempt to match the patient's specific femoral or tibial geometry, thus reducing their chances for optimal success. Because these devices were made of CoCr, which has different viscoelastic and wear properties from the natural articular materials, any surface geometry which did not closely match the bearing surface of the tibia or femur could cause premature wear of the remaining cartilage due to asymmetric loading.

Newer materials technologies in development including filling the joint space by injecting polyurethane (U.S. Pat. No. 5,795,353) into the joint and anchoring it with holes drilled into the tibial plateau. Others include a series of polymeric materials such as PVA hydrogels in a titanium mesh (see Chang et al, *Journal of Biomedical Materials Research* 37, 51-59, 1997), biodegradable anhydride prepolymers that can be cross-linked with irradiation by UV light (U.S. Pat. No. 5,902,599), and in vivo grown articular chondrocytes in a collagen fiber or other biocompatible scaffold (U.S. Pat. No. 5,158,574). Other low surface energy materials, such as low temperature isotropic (LTI) pyrolitic carbon, have been investigated as bearing surfaces as well. However, these techniques are limited by one's ability to first of all fashion these materials in a conformal manner to replicate the existing knee geometry, while at the same time maintaining their location within the joint, while further being able to survive the mechanical loading conditions of the knee.

U.S. Pat. Nos. 6,206,927 and 6,558,421 and copending U.S. application Ser. No. 10/232,608, each of which are incorporated by reference herein, disclose a prosthesis for the knee compartment which fills the joint space in order to replace the missing articular materials. This prosthesis provides an anatomically correct bearing surface for both the tibial plateau and femoral condyle to articulate against. Additionally, the prosthesis reduces the concentrated loads on the femoral condyle and its articular cartilage and maintains proper spatial location of the femoral condyle to the tibial plateau, thereby restoring normal joint alignment. Advantageously, the prosthesis does not require any bone resection or any means of bone fixation.

In addition to these benefits, it is also desired to provide a unicompartmental prosthesis which has improved load absorbing characteristics, provides improved load carrying ability throughout the complete range of motion (ROM), and increases patient comfort.

SUMMARY OF THE INVENTION

Accordingly, a prosthesis is provided for implantation into a body joint, such as the knee joint compartment between a femoral condyle and its corresponding tibial plateau, without requiring bone resection. The prosthesis includes a body having a generally elliptical shape in plan and a pair of opposed surfaces where one of the surfaces is generally concave. The body further includes an exterior portion and an interior portion, where the exterior portion is constructed from a higher modulus material than the interior portion, such that the body is at least slightly deformable.

According to one embodiment of the present invention, the interior portion is hollow. According to another embodiment, the interior portion is preferably constructed from materials such as reinforced and non-reinforced elastomeric polymers, viscous-elastic materials, and hydrogels. The exterior portion is preferably constructed from materials such as ceramics, metals, metal alloys, hydrogels, and reinforced and non-reinforced thermoset or thermoplastic polymers, or composites thereof. Either the exterior portion or the interior portion can be constructed at least partially from a polymer capable of containing living cells, and can include an active material associated therewith. The exterior portion can include a surface coating, such as for reducing friction of the prosthesis.

A locking mechanism can be disposed in the interior portion and arranged to connect the pair of opposed surfaces to enhance the integrity of the prosthesis. In a preferred embodiment, the locking mechanism includes a first mating component affixed to one of the opposed surfaces and a second mating component affixed to the other opposed surface and arranged to be securely received by the first mating component. The first and second mating components can preferably move relative to one another.

In further accordance with a preferred embodiment of the invention, the pair of opposed surfaces includes a top surface that is generally concave and a bottom surface that is generally flat. A peripheral edge extending between the top and bottom surfaces and includes a first side, a second side opposite the first side, a first end, and a second end opposite the first end. A first dimension D is defined by the first end and the second end, and a second dimension F is defined by the first side and the second side, wherein the dimension F is from about 0.25D to about 1.5D. Both the top and bottom surfaces are preferably contoured such that the prosthesis is self-centering within the knee joint compartment.

According to the present invention, outside edges along a periphery of the body are rounded. A periphery of the body is on average of greater thickness than a central portion of the body, and preferably a section across the body from the first end to the second end generally has the shape of a negative meniscus. In a preferred embodiment, a section across the body from the first side to the second side has a thickness at a periphery of the first side which is larger on average than a thickness at a periphery of the second side. The body is preferably free of any means of fixation within the knee joint compartment, but can alternatively be arranged to be constrained within the knee joint compartment.

Correspondingly, a method is provided for implantation of a prosthesis into a knee joint compartment between a femoral condyle and its corresponding tibial plateau without requiring bone resection. The method includes providing a prosthesis including a body having a generally elliptical shape in plan and a pair of opposed surfaces where one of the surfaces is generally concave, the body having an exterior portion and an interior portion wherein the exterior portion is constructed from a higher modulus material than the interior portion. The method further includes surgically exposing the knee joint compartment and inserting the prosthesis into the knee joint compartment.

In further accordance with the present invention, the method can further include determining a size and shape of the prosthesis required by examination of the knee joint, where the examination can include X-ray imaging or MRI imaging. The prosthesis can be selected from a library of prostheses of standard shapes and sizes, or alternatively a custom prosthesis can be generated where the size and shape are at least partially based on the examination of the knee joint. If necessary, the condition of tissue located in the knee joint compartment or in adjacent areas can be altered, and an active material can be associated with the body. The prosthesis is preferably pre-loaded during implantation.

In further accordance with the present invention, a method is provided for correcting misalignment in an axis of rotation of a knee joint. The method includes providing a prosthesis including a body having a generally elliptical shape in plan and a pair of opposed surfaces wherein one of the surfaces is generally concave, the body having an exterior portion and an interior portion wherein the exterior portion is constructed from a higher modulus material than the interior portion. The method further includes surgically exposing the knee joint, and inserting the prosthesis into the knee joint to at least partially correct the misalignment of the axis of rotation. The method can include inserting the prosthesis into a medial compartment of the knee joint and moving the axis to a less varus condition, or can include inserting the prosthesis into a lateral compartment of the knee joint and moving the axis to a less valgus condition.

The above features and advantages, along with other features and advantages of the present invention are readily apparent from the following detailed description of the best mode for carrying out the invention when taken in connection with the accompanying drawings.

DETAILED DESCRIPTION OF THE PREFERRED EMBODIMENT(S)

Figure 1:
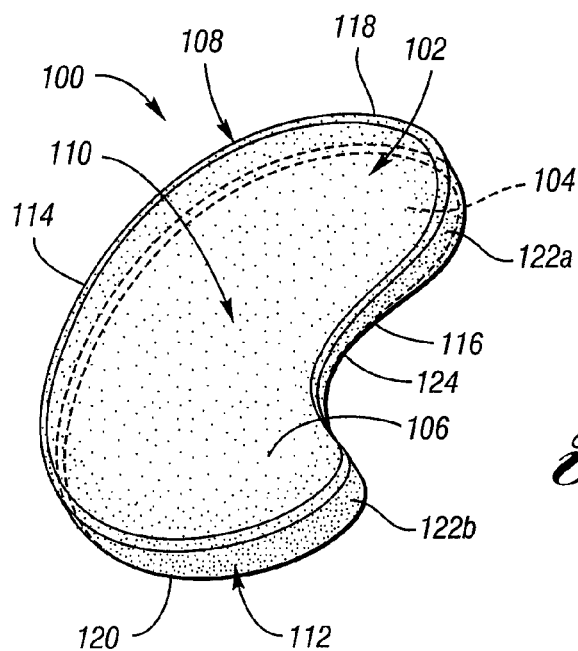
FIG. 1 is a perspective view illustrating an implantable knee prosthesis according to the present invention.

The prosthesis according to the present invention is designed to be surgically implantable into a body joint to replace damaged tissue therein. More particularly, the prosthesis of the present invention is a unicompartmental device suitable for minimally invasive, surgical implantation into a knee compartment without requiring bone resection. The knee compartment is defined by the space between a femoral condyle and the respective tibial plateau, in which a portion of the natural meniscus is ordinarily located. By effectively replacing worn articular material, the prosthesis of the present invention restores the normal joint alignment and provides a smooth bearing surface against which the femoral condyle can articulate. Degeneration of the femoral anatomy is significantly reduced because the conforming femoral surface of the prosthesis accommodates the complex shape of the femoral condyle in extension as well as in flexion. Further, it essentially eliminates articulation of the femoral condyle against the tibial plateau, thereby preventing further degradation of the tibial surface. By occupying the joint space and retensioning the collateral ligaments, the prosthesis according to the present invention improves joint stability and restores the limb to a more normal mechanical alignment.

By the term "unicompartmental" it is meant that each prosthesis according to the present invention is suitable for implantation into but one medial or lateral compartment defined by the space between a femoral condyle and its associated tibial plateau. In other words, the present prosthesis is not a bicompartmental prosthesis which, in one rigid device, could be inserted into both of the two femoral condyle/tibial plateau compartments. In many, if not most, cases a prosthesis will be inserted into one compartment only, either the medial or lateral compartment. Most often, it will be the medial compartment as the meniscus and associated articular surfaces in the medial compartment are most subject to wear and damage. Additionally, it is possible to insert two separate prostheses into the medial and lateral compartments of the same knee, or to use two such prostheses that are mechanically, but non-rigidly, linked. Advantageously, the prosthesis according to the present invention functions to at least partially correct misalignment in the knee axis of rotation due to disease. More specifically, when placed in the medial compartment, the prosthesis moves the knee axis 300 (see FIG. 10) into a less varus, more valgus condition (typically 0-5° valgus). Likewise, when placed in the lateral compartment, the prosthesis moves the knee axis 300 into a less valgus condition.

The prosthesis according to the present invention is preferably translatable but self-centering. By "translatable" it is meant that during natural articulation of the knee joint the prosthesis is allowed to move or change its position, such that articulation of the knee results in a modest amount of lateral/medial and anterior/posterior translation of the prosthesis relative to the tibial plateau. Thus, the present prosthesis preferably is devoid of means of physical attachment which limit its movement, for example, screws, mating ridges and depressions, porous areas to accommodate tissue regrowth, and the like.

The femoral condyle has two major anterior/posterior radii such that, when the knee is in full extension, one radius position is in contact with the tibial plateau while, during flexion, another portion of the femoral condyle is in contact with the tibial plateau. In addition, the femur rotates with respect to the tibia during flexion, thereby changing the orientation of the femoral anatomy to the tibial plateau. The term "self-centering" means that upon translation from a first position to a second position during knee articulation, the prosthesis of the present invention will return to substantially its original position as the articulation of the knee joint is reversed and the original knee position is reached. Thus, the prosthesis will not progressively "creep" towards one side of the compartment in which it is located, but rather the prosthesis is shaped such that the contour of the prosthesis and the natural articulation of the knee exerts a restoring force on the free-floating prosthesis. The angle of attack of the femoral condyle and/or tibial plateau bearing surfaces against the prosthesis will ensure that the prosthesis reversibly translates during articulation, maintaining the prosthesis, on average, in the same location for any given degree of knee articulation. The centered, rest position, of the prosthesis is usually determined when the knee is in extension and there is maximum contact between the femoral condyle and the prosthesis. In order to ensure the ability of the prosthesis to "self-center," adequate tension of the cruciate ligaments should be maintained.

While the prosthesis according to the present invention is shown and described herein as being implanted in a knee joint, it is understood that the prosthesis could be utilized in joints other than the knee, such as the hip, shoulder, wrist, ankle, or elbow.

Turning now to FIGS. 1-4, an implantable knee prosthesis 100 according to the present invention is illustrated. Prosthesis 100 includes a body 102 having a generally elliptical shape in plan and including a bottom, or tibial, surface 104 and an opposite top, or femoral, surface 106. Bottom surface 104 is preferably generally flat and top surface 106 is preferably generally concave. However, it is understood that other contours of top and bottom surfaces 104, 106 are fully contemplated in accordance with the present invention. For example, depending on the condition of the ligaments and other soft tissue structure at the time of surgery and how much stability the knee will require, for a medial compartment implantation top surface 106 typically ranges from generally flat to concave and bottom surface 104 typically ranges from generally flat to convex. For a lateral compartment implantation, top surface 106 can range from generally convex to generally concave and bottom surface 104 typically ranges from generally flat to concave. It is also understood that the terms "concave" and "convex" as used herein are not restricted to describing surfaces with a constant radius of curvature, but rather are used to denote the general appearance of the surfaces.

With continued reference to FIGS. 1-4, body 102 further includes a peripheral edge 112 extending between bottom surface 104 and top surface 106 and having a first side 114, a second side 116 opposite first side 114, a first end 118, and a second end 120 opposite first end 118. As shown, edges along the periphery of prosthesis 100 are rounded rather than presenting sharp corners, such as in those devices of U.S. Pat. No. 5,158,574. This rounded periphery is desired due to the fact that prosthesis 100 is preferably allowed to move within the joint cavity. Periphery 108 of body 102 is on average of greater thickness than a central portion 110 of body 102 (see FIG. 1), and preferably body 102 generally has a negative meniscus shape when viewed from the side (see FIG. 3) or in a section across body 102 in an anterior-posterior direction from first end 118 to second end 120 (see, for example, FIG. 6). Furthermore, in a preferred embodiment, a section across the body in a medial-lateral direction from first side 114 to second side 116 has a thickness at a periphery of first side 114 which is larger on average than a thickness at a periphery of second side 116 (see FIG. 7).

In the embodiment depicted herein, second side 116 of body 102 includes a pair of lobes 122a and 122b, where lobe 122a is adjacent first end 118 and lobe 122b is adjacent second end 120, with an indentation 124 formed therebetween. When implanted in a patient's knee compartment (see FIG. 10), indentation 124 will be proximate to the tibial spine and can preferably be designed to vary in shape from patient to patient as necessary due to the great range of variability of human anatomy. With indentation 124, prosthesis 100 is generally kidney-shaped when viewed in plan, with the shape resembling a distorted ellipse. Of course, indentation 124 is not required, and other variations of body configuration are fully contemplated according to the present invention. Accordingly, it is understood that the term "generally elliptical" is intended to include all construction methods which yield a generally planar shape which is longer in one direction than in the transverse direction and has rounded corners, and that prosthesis 100 is not otherwise limited to any particular shape.

Figure 2:
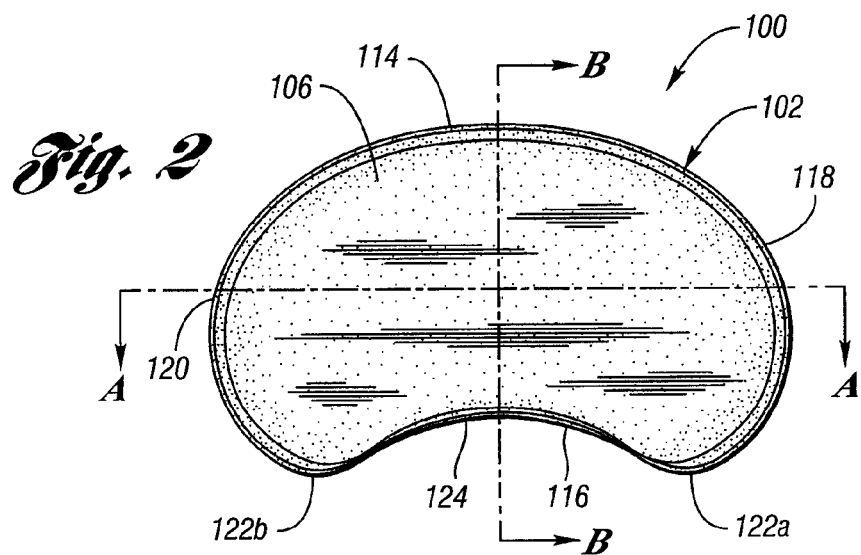
FIG. 2 is a top plan view of the prosthesis of FIG. 1.
Figure 3:
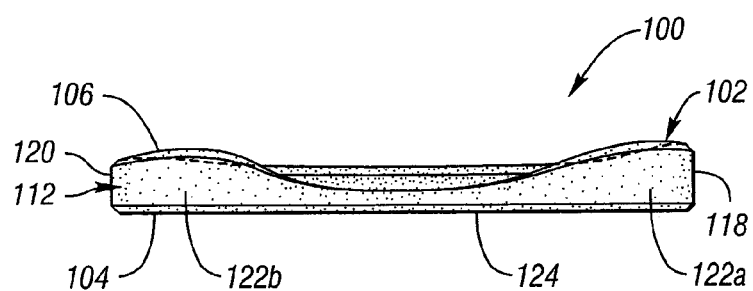
FIG. 3 is a side elevational view of the prosthesis of FIG. 1.
Figure 4:
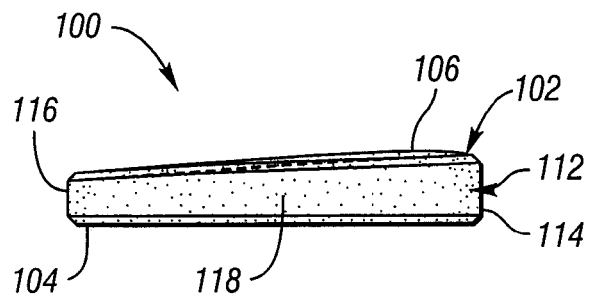
FIG. 4 is an end elevational view of the prosthesis of FIG. 1.
Figure 5:
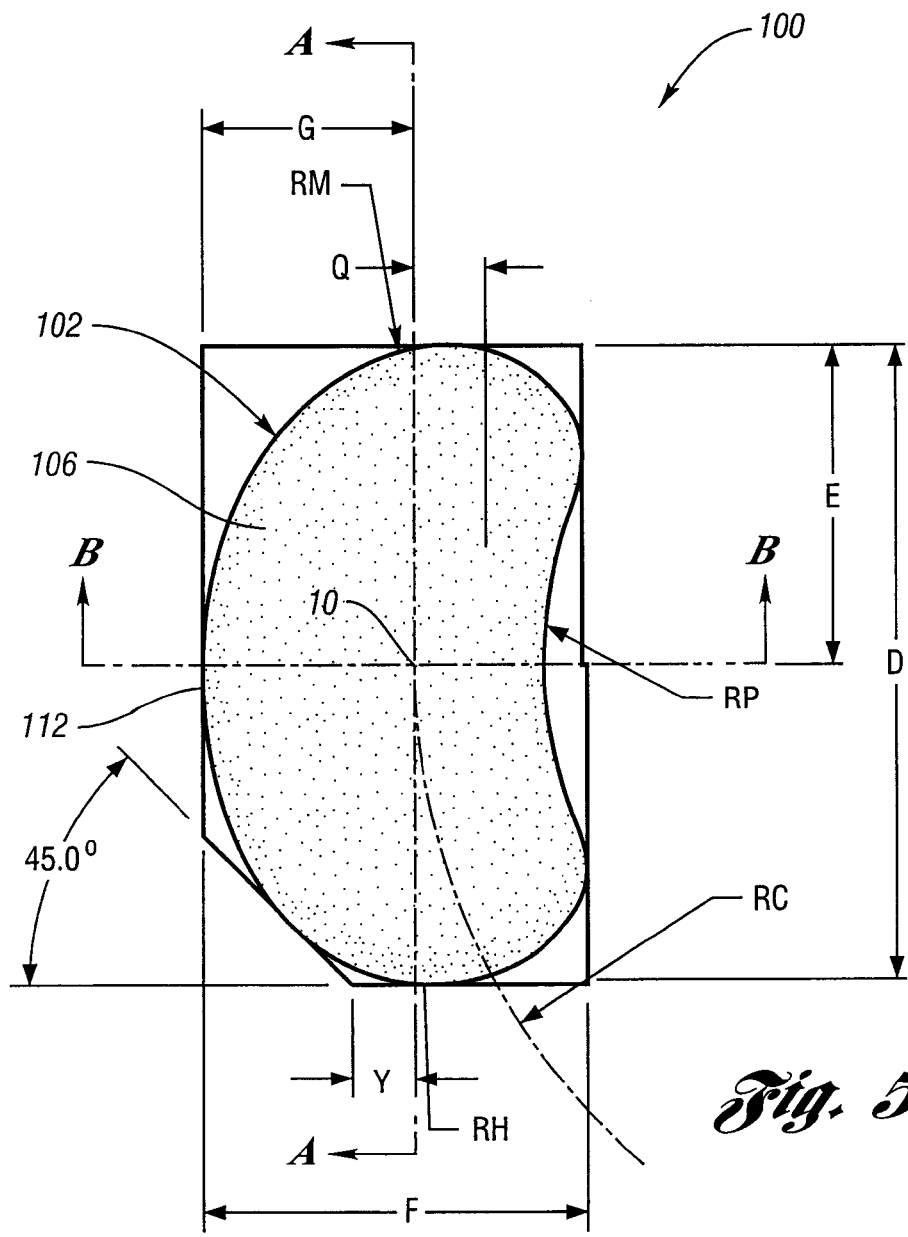
FIG. 5 is a top plan view of the prosthesis according to the present invention with reference to a coordinate system.
Figure 6:
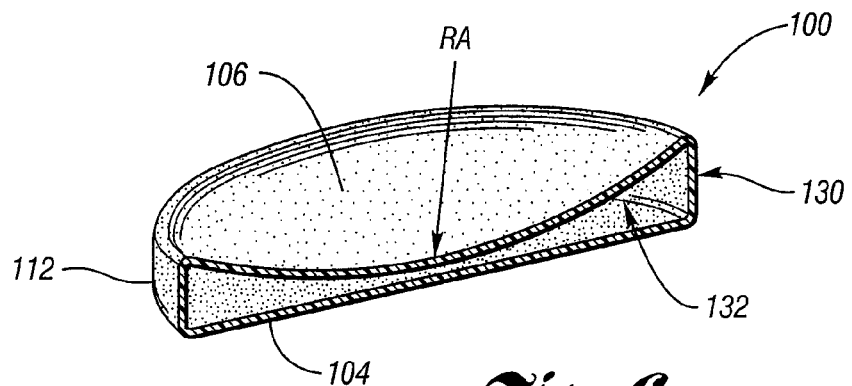
FIG. 6 is a cross-sectional view of a first embodiment of the prosthesis taken along line A-A of FIG. 5.
Figure 7:
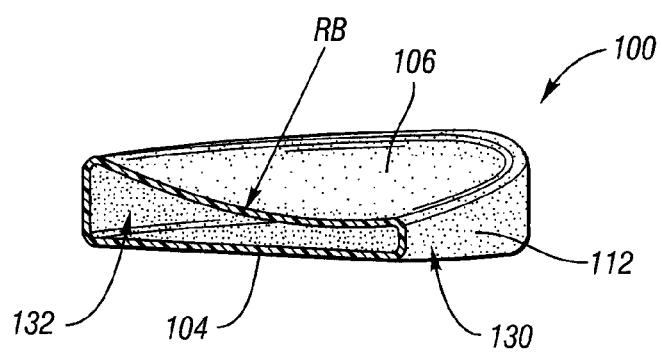
FIG. 7 is a cross-sectional view of a first embodiment of the prosthesis taken along line B-B of FIG. 5.
Figure 8:
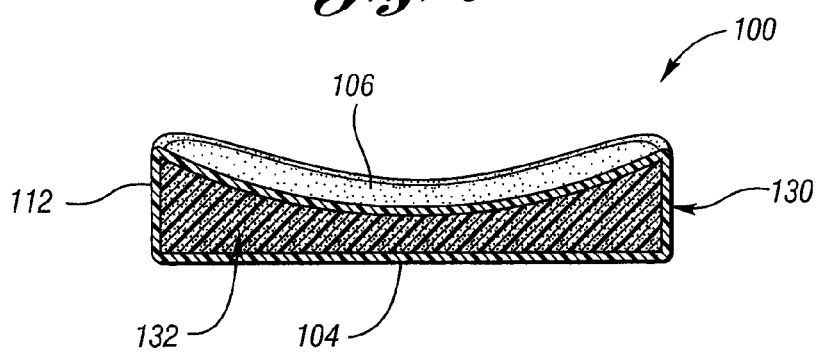
FIG. 8 is a cross-sectional view of a second embodiment of the prosthesis taken along line A-A of FIG. 5.
Figure 9:
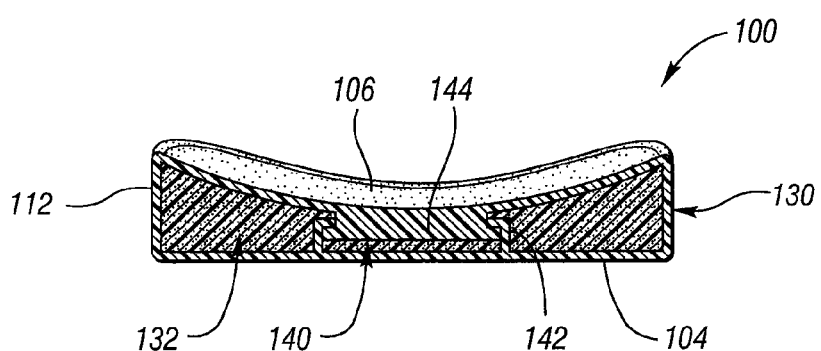
FIG. 9 is a cross-sectional view of a third embodiment of the prosthesis taken along line A-A of FIG. 5.

FIGS. 6 and 8-9 show an anterior/posterior cross-sectional view of prosthesis 100 taken along section line A-A of FIGS. 2 and 5. Similarly, FIG. 7 illustrates a medial/lateral cross-sectional view of prosthesis 100 taken along section line B-B of FIGS. 2 and 5. As shown in FIGS. 6 and 7, prosthesis 100 includes an exterior portion 130 and an interior portion 132. Exterior portion 130, which includes bottom and top surfaces 104, 106, comprises a relatively high modulus material as compared with interior portion 132, wherein the material is also preferably low friction. Materials suitable for the construction of exterior portion 130 include, for example, metals such as steel or titanium, metal alloys such as those described in U.S. Pat. Nos. 3,989,517; 5,368,659; and 5,618,359 (LiquidMetal, Inc.), ceramics, hydrogels, and reinforced and non-reinforced thermoset or thermoplastic polymers. The hardness of the material for exterior portion 130 should be sufficient to span defects in the tibia or femur without substantially deforming into the defects, allowing for the provision of recessed or non-contacting areas of the prosthesis to encourage articular regeneration.

Exterior portion 130 need not be made only of a single material, but composite structures may be used. Other possible materials are those which can replicate the function of naturally occurring cartilage or meniscus such as the CSTI meniscal repair material that is the subject of numerous U.S. patents to Stone, for example, U.S. Pat. No. 5,158,574. A surface coating on exterior portion 130 can be utilized, such as for the reduction of friction of prosthesis 100. Generally, the areas of exterior portion 130 expected to have the most wear due to either high stress or greater movement relative to the femoral condyle or tibial plateau may be made of stronger, more abrasion resistant material than the remainder of prosthesis 100 when composite structures are used. However, it is understood that any single component may be softer than the material used for constructing the majority of exterior portion 130.

In contrast, interior portion 132 comprises a lower modulus material as compared with exterior portion 130, where interior portion 132 is at least slightly deformable in order to absorb load energy. Depending upon the specific materials used for exterior portion 130 and interior portion 132, the relative thicknesses and proportions of exterior portion 130 and interior portion 132 are chosen to allow this deformability, but are not otherwise limited to any specific configuration. In a preferred embodiment, the ratio of interior portion thickness to exterior portion thickness is about 10:1. With reference to FIG. 8, suitable material choices for interior portion 132 include hydrogels, elastomeric polymers such as nylon, silicone, polyurethane, polypropylene, polyester, or the like, optionally fiber-reinforced, viscous-elastic materials, as well as other hydrophilic materials or hydrophobic materials. Alternatively, interior portion 132 can be hollow as depicted in FIGS. 6 and 7.

The hard yet deformable nature of prosthesis 100 of the present invention advantageously accommodates both the conformal fit that a matched component offers in an ideal knee and the mismatch that often occurs when one introduces patient specific kinematic ROM such as femoral roll-back and differing amounts of medial pivot or lateral pivot-shift mechanisms into the "real world" equation. The intact meniscus carries 50-90% of the total load in a medial knee joint, and prosthesis 100 of the present invention accomplishes load absorption through deformation as well as movement. Importantly, prosthesis 100 can mimic the conformal meniscal behavior not just in extension, but throughout the range of motion, thereby reducing wear and load on the remaining articular surfaces and increasing patient comfort.

Prosthesis 100 of the present invention can include a locking mechanism 140, such as that shown in the cross-sectional view of FIG. 9, which interlocks the bottom and top surfaces 104, 106 together to maintain the integrity of the prosthesis 100, such as in the hollow embodiment of FIGS. 6 and 7 or in case of breakdown of the load absorbing material (see FIG. 8) in interior portion 132. Preferably, locking mechanism 140 comprises a first mating component 142 affixed to an interior side of bottom surface 104, and a second mating component 144 affixed to an interior side of top surface 106 and arranged to be securely received by first mating component 142. Locking mechanism 140 is preferably constructed of the same material as exterior portion 130 and molded integrally therewith. With this configuration, components 142, 144 of locking mechanism 140 can move relative to one another to allow deformation of prosthesis 100 during use, yet still limit the maximum spacing of surfaces 104, 106. Of course, it is understood that locking mechanism 140 and its components 142, 144 could have a different structure other than that depicted herein. Furthermore, locking mechanism 140 could alternatively comprise a solid connection between bottom and top surfaces 104, 106.

In accordance with the present invention, prosthesis 100 may be manufactured so as to substantially contain, or have deposited thereon, a biologically or pharmaceutically active material such as, for example, one that promotes tissue regrowth, retards tissue degeneration, or decreases inflammation. This is particularly suitable when prosthesis 100 functions to bridge a defective area of bone or articular cartilage. The active material can be provided in the form of a coating on exterior portion 130, or can be contained within exterior portion 130 or interior portion 132 in the form of a solid, liquid, gel, paste, or soft polymer material. Such active materials may be designed to be delivered at once or in a timed-release manner. Preferably, the area of prosthesis 100 containing the active material does not actually contact, or minimally contacts, the damaged tissue. In addition, exterior portion 130 or interior portion 132 can be constructed of a material, such as a biocompatible polymer, capable of containing living cells.

As stated above, one purpose of the prosthesis 100 of the present invention is to achieve a span-like effect to bridge areas of the femoral condyle and/or tibial plateau which have been damaged or have experienced tissue degeneration. If too soft and/or low modulus of a material were to be used for the entire prosthesis as in prior art devices, not only would the load not be concentrated on healthy tissue, but damaged areas would also be subjected to static and dynamic loading and wear, thereby decreasing the opportunity for the body's natural regenerative capability to function. Under such circumstances, active materials will be rapidly dissipated and newly regenerated articular cartilage not having the necessary density or cohesiveness to withstand wear will quickly be eroded away. Rather than substantially deforming as in prior art devices to distribute a load relatively equally on the mating femoral and tibial surfaces, prosthesis 100 according to the present invention does not necessarily spread the load uniformly, but rather may redistribute the load to healthy tissue, spanning areas of imperfection and allowing inflamed, diseased, or other damaged areas to regenerate. Moreover, as regeneration proceeds, the regenerating tissue will assume a shape dictated by the shape of prosthesis 100. Growth under these circumstances has the greatest potential for dense, ordered cartilage most closely replicating the original surface.

Prosthesis 100 is preferably allowed to be mobile, accommodating a wide variety of patient kinematic types. However, the forces required to deform the prosthesis 100 must be balanced with the forces attempting to move the prosthesis 100 from its position on the tibia. These forces are present regardless of whether the prosthesis 100 is fixed to the tibia or not. Thus, while prosthesis 100 is described herein as being mobile, it is fully contemplated that prosthesis 100 could easily be converted to an embodiment in which its movement is constrained by attachment to the tibia, the surrounding synovial membrane, meniscal remnants, or the like. In this embodiment, the intent is not necessarily to fix prosthesis 100 in one permanent location, but rather to limit its motion in order to balance motion of prosthesis 100 with deformation and load absorption and also as a means of preventing dislocation.

Much study has been dedicated to determine if any relationship exists in the normal human anatomy that would allow one to define the required dimensions of the prosthesis for proper fit and function based on a single, easy to establish, measurable anatomic landmark. Based on a study of over 100 MRI's and 75 X-rays of human subjects ranging from 15 to 87 years of age, a relationship was established between the anteroposterior radius of the most distal portion of the femoral condyle and the dimensions which control the geometric form of the prosthesis. The database revealed a range of femoral anteroposterior radii from 32 mm to 48 mm. However, it is known that the worldwide range is much larger because of genetic differences in the human anatomy.

With reference now to FIG. 5, a preferred method of construction of the prosthesis 100 of the present invention aligns the apex of a femoral radius with the Coordinate System Origin (CSO) 10. The apex of a tibial surface is also generally aligned in both the anterior/posterior with the CSO 10, but is separated vertically from the CSO 10 to create the part thickness. The substantially elliptical shape of peripheral edge 112 is then located with respect to the CSO 10. In general, the CSO 10 of the prosthesis 100 is located at the center of the ellipse. It has been found that a suitable size for body 102 is defined by a minor axis of the ellipse F (defined by first side 114 and second side 116) and a major axis D (defined by first end 118 and second end 120) which are related by a ratio ranging from F=0.25D to 1.5D. Similar ratios can be established for all of the controlling dimensions of the part such that the shape in plan, femoral surface geometry, and tibial surface geometry for a normal tibial anatomy can generally be defined by one physical anterior/posterior measurement of the patient's tibial anatomy. The appropriate thickness of the prosthesis 100 can be determined by measuring the amount of joint space between the femoral and tibial surface when a minor amount of valgus (heels out, knees in) is applied to the knee.

Referring to FIGS. 5-7, the preferred relationship between femoral radius RA (see FIG. 6) to other joint dimensions (femoral radius is the driving relationship to all other dimensions) is as follows:

Medial-lateral radius RB=0.25RA to 1.0RA (see FIG. 7)
Curve of anterior half of femoral radius RC=0.5RA to 2.0RA, posterior half is straight
Length D=0.6RA to 1.4RA
Posterior half E=0.1RA to 0.75RA
Width F=0.25RA to 1.5RA
Width from part center to medial edge G=0.096RA to 0.48RA
Anterior plan radius RH=0.16RA to 0.64RA
Posterior plan radius RM=0.16RA to 0.64RA
Radius along lateral spine area RP=0.1RA to 2.0RA
Width from part center to lateral edge Q=−0.32RA to 0.32RA
Location of transition from anterior radius to medial radius Y=−0.32RA to 0.32RA (A negative value means that a dimension may extend to an opposite side of section line A-A).

The actual shape of the prosthesis 100 may be tailored to the individual. Individuals with high varus or valgus deformation due to wear, degeneration, or disease may require a prosthesis which is of considerably greater thickness over the portions where wear is most advanced. In youthful patients, where trauma-induced damage rather than severe wear or degeneration has occurred, differences in prosthesis thickness will be more moderate.

The axis of rotation of the tibia on the femur is 90 degrees to the path of the tibial plateau against the femoral condyle. The two tibial plateaus (medial and lateral) are not in the same plane with each other but do act in a relatively constant radius to their respective femoral condyles. In other words, although the symmetry of the femoral side of the prosthesis may be matched with the femoral condyle while the leg is in full extension, the rotation of the tibial plateau against the femoral condyle is along a constant axis of rotation (90 degrees to the axis of rotation), thus the angularity of the axis of symmetry of the femoral condyle relative to the axis of symmetry of the tibial plateau is not parallel but at some acute angle. Also, the axis of symmetry of the tibial plateau is not parallel to the path of rotation of the tibia relative to the femur, but also at some mildly acute angle. Thus, the true orientation of the prosthesis, regardless of the relative orientations of symmetry of the tibial side to the femoral side is 90 degrees to the true axis of rotation as described in Hollister et al., "The Axes of Rotation of the Knee," Clin Orthopaedics and Rel Res 290, pp. 259-268, 1993, herein incorporated by reference. Any localized positions of higher loads are self-limiting due to the ability of the prosthesis to translate both rotationally and laterally which mimics the true motion of the natural meniscus as described by Hollister.

During the load bearing portion of the gait cycle, or stance phase, flexion at the knee does not typically exceed 35°. Thus, the highest compressive loads in the knee occur with the knee substantially extended. The outer contours of the prosthesis are therefore preferably designed to substantially mate with the corresponding tibial and femoral surfaces when the knee is in full extension so that the high compressive loads can be distributed over large surface areas. The contact areas between the femoral condyle and the femoral surface of the prosthesis and between the tibial plateau and the tibial surface of the prosthesis are substantially equivalent during extension. However, because the contour of the femoral surface is more concave, the femoral condyle determines the position of the prosthesis on the surface of the tibial plateau in extension.

As the knee is flexed, the mating along the tibial surface is substantially maintained. However, the contoured mating surfaces of the femoral condyle and femoral surfaces of the prosthesis of the present invention can become increasingly dissimilar when the joint articulates. As the knee is flexed, there is a relative external rotation and posterior translation of the femur with respect to the tibia. Thus, the contour angle of the femur becomes more in-line with the contour angle of the tibia in flexion. This can cause relative lateral or rotational movement, in the tibial plane, between the femoral condyle and the femoral surface of the prosthesis. The forces generated by the increasingly different geometry creates a rotational moment in the tibial plane which is resisted along the mating tibial surfaces and which also results in a restoring force tending to correctly locate the prosthesis along the femoral condyle. Thus, the prosthesis is self-centering to the femoral condyle, in part as a result of the conformity between the femoral condyle and the femoral surface of the prosthesis.

By changing the femoral surface of the prosthesis, it is possible to reduce the rotational moment induced during flexion by the mismatch between the femoral surface of the prosthesis and the femoral condyle. A preferred method to accommodate this motion is to have a less acute alignment between the femoral and tibial axes of symmetry posterior to the anterior/posterior midline, thereby reducing the mismatch between the two axes in flexion. This angle is preferably 0° and can range from +/−15°. Anterior to the midline, the femoral contour is bent around a radius RC that is tangent to the posterior section of the sweep plane at the most distal point of the femoral anterior/posterior radius RA. This femoral surface geometry is essentially a compromise between the different extension and flexion alignments of the femoral and tibial axes of symmetry.

Because the prosthesis 100 according to the present invention preferably has no physical method of attachment, the generally concave femoral surface serves to locate the prosthesis through all ranges of motion. Of course, it is understood that proper tensioning of the collateral ligaments is also important to maintain positioning of the prosthesis. By the very nature of the ability to adjust for the lost articular material through the thickness of the prosthesis, the thickness adjustment substantially eliminates the need for a functional meniscus as a bearing surface in a severely (Grade III or IV) degenerated knee. In these instances, the femoral surface of the prosthesis resides significantly above the meniscal edge, and the meniscus is completely unloaded.

The prosthesis according to the present invention also increases the translational stability of the knee. The conforming shape of the femoral surface limits excessive anterior to posterior translation of the femur. As a result, this prosthesis possibly eliminates the need for ACL reconstruction in the older patient.

Figure 11:
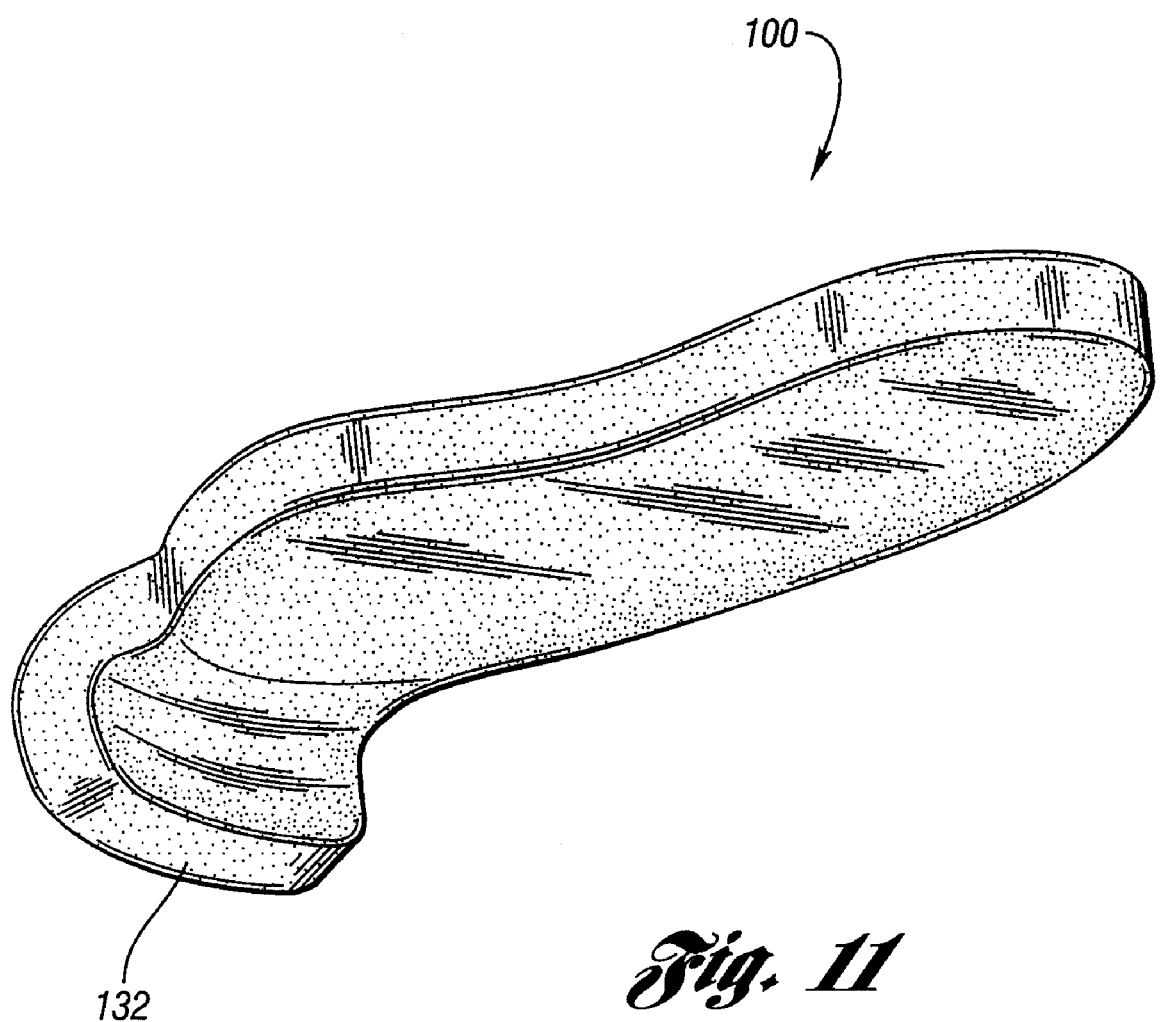
FIG. 11 is a perspective view of a prosthesis according to the present invention which includes a cusp.

In some cases is may be necessary to add "reverse (downward)" curves, or cusps 132, to prosthesis 100 as shown in FIG. 11, located along the lateral aspect (of a medial device) of the device at the extreme anterior/lateral and posterior/lateral protrusions. Such circumstances would be when there is deformed anatomy or additional stabilization is required of prosthesis 100.

Generally speaking, each knee presents a different geometry of the respective femoral condyles and tibial plateaus. Even with respect to the right and left knees of a single individual, although bilateral symmetry dictates that the left and right knee components should be mirror images, this is often only an approximation. Thus, the shape of the affected femoral condyle and tibial plateau (while discussed herein in the singular, more than one pair of condyle(s)/plateau(s) may be involved), will have to be ascertained to determine the correct geometry of the prosthesis 100 for a given patient.

To implant a prosthesis that possesses the characteristics required by the subject invention, the patient's knee joint may be examined by a non-invasive imaging procedure capable of generating sufficient information such that one appropriately sized and shaped device may be selected. A variety of non-invasive imaging devices may be suitable, for example magnetic resonance imaging (MRI), X-ray devices and the like.

Two methods of non-invasive imaging for selection of a suitable prosthesis 100 are preferred. In the first method, MRI or other non-invasive imaging scans, optionally coupled with exterior measurements of the dimensions of the relevant tibial and femoral portions including the surface of the articular cartilage of the tibia and femur, may be used to establish a library of prostheses whose size and geometry differ according to the age and size of the patient, the patient's genetic make-up, and the like. A limited number of "standard" prostheses are then made to meet the requirements of a generic population of patients. In this first method, a non-invasive imaging scan, such as an X-ray or MRI, together with knowledge of the patient's genetic make-up, general body type, extent of the disease, degeneration, or trauma and the like, will enable the surgeon to select a prosthesis 100 of the correct size and shape from the library for the patient.

In a second method, each patient receives one or more prostheses that are custom tailored for the individual by producing a contour plot of the femoral and tibial mating surfaces and the size of the meniscal cavity. Such a contour plot may be constructed from imaging data (i.e., X-ray or MRI data) by a suitable computer program. From the contour plot, the correct surface geometry of the prosthesis 100 is determined from the shape of the respective tibial plateau and femoral condyle and the orientation between the two surfaces in extension. In general, the shapes just mentioned also include the articular cartilage which is typically maintained substantially intact.

In accordance with the present invention, it has been discovered that the amount of varus deformity is the primary, non-invasive method for determining the necessary thickness of the prosthesis 100 required for proper functioning. Viewing a weight bearing anteroposterior X-ray, a cut and paste of the line drawn through the femoral condyles and repositioned to put them once again parallel to the tibial plateaus will yield a measurement for the approximate thickness of the prosthesis. However, typically the proper thickness of the prosthesis is determined intra-operatively.

Insertion of the prosthesis 100 of the present invention is typically done via a 3 cm to 5 cm medial parapatella incision. The prosthesis 100 is introduced by arthroscopically assisted implantation, generally limited to extensive clean-up of existing damaged tissue, e.g., torn or particulate natural meniscus damage, osteophyte resection, etc. The natural meniscus may be maintained in position or may be wholly or partially removed, depending upon its condition. Under ordinary circumstances, pieces of the natural meniscus which have been torn away are removed, and damaged areas may be trimmed as necessary. In somewhat rarer instances, the entire portion of the meniscus residing in the meniscal cavity may be removed or is not present. No bone resection or mechanical fixation of the prosthesis 100 is required. Only osteophytes which interfere with the prosthesis placement or with proper collateral ligament alignment are removed.

Prosthesis 100 may also be used in conjunction with ACL or PCL repair, tibial osteotomy or articular surfacing procedures such as cartilage transplantations or abrasion anthroplasty. Following insertion of the prosthesis, X-ray, fluoroscopy, or MRI may be used to assess the correct positioning of the prosthesis both intraoperatively as well as postoperatively. Since the surgical procedures used are not severe, and also not irreversible, an unsuitable prosthesis may be readily removed and replaced, either with a different prosthesis from the library, or by a custom prosthesis.

Prosthesis 100 of the present invention is preferably preloaded in a compressed state during implantation. Thus, if the joint is temporarily unloaded during periods of exercise, the expandability of the prosthesis of the present invention advantageously allows the prosthesis to maintain contact with both condylar and tibial surfaces throughout the ROM.

Figure 10:
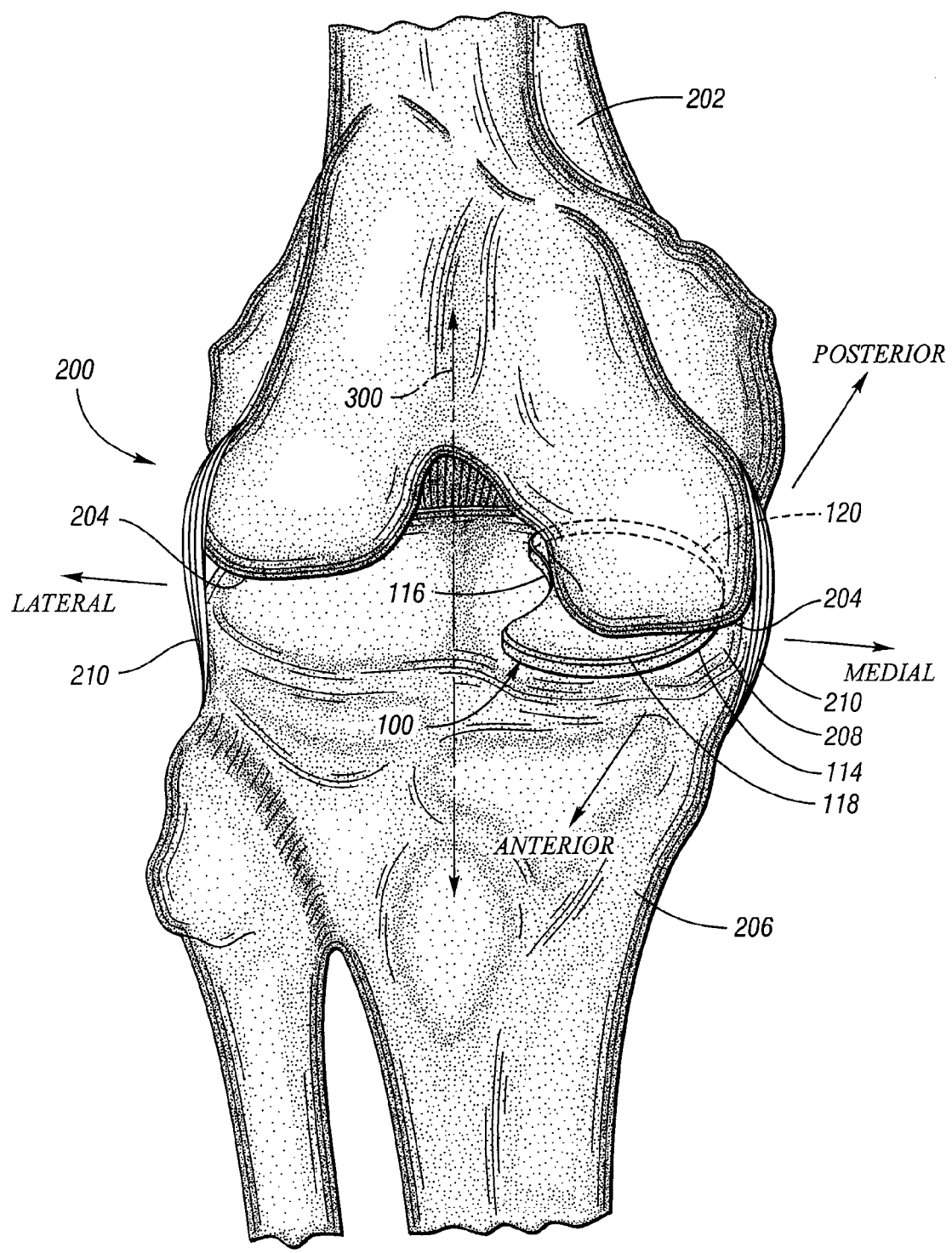
FIG. 10 illustrates an exemplary placement of the prosthesis according to the present invention in a knee joint.

FIG. 10 illustrates prosthesis 100 positioned in a right knee joint 200 between a femur 202, including the femoral condyles 204, and a tibia 206 including the tibial plateau 208. The femur 202 and tibia 206 include interconnecting collateral ligaments 210. FIG. 10 illustrates the position of first side 114, second side 116, first end 118, and second end 120 of prosthesis 100 when inserted in the medial compartment of a patient' right knee joint 200. Of course, prosthesis 100 according to the present invention may just as easily be implanted in a lateral compartment or in the left knee of a patient.

One preferred surgical procedure which may be used to implant the prosthesis 100 according to the present invention can be described by the following steps:

1. Verify preoperative indications:
    a. Valgus determination of <5° with erect anterior/posterior X-ray;
    b. Medial compartment disease only. Some lateral spurs may be present; and
    c. Pre-operative sizing via medial/lateral template measurement of anterior/posterior X-ray.
2. Standard Arthroscopy surgical prep:
    a. Infiltrate knee with Lidocaine/Marcaine and Epinephrine.
3. Arthroscopy:
    a. Inspect lateral patello-femoral compartments for integrity, some mild arthosis is acceptable;
    b. Removal of medial meniscus toward the rim along the anterior, medial and posterior portions;
    c. Initial arthroscopic osteophyte removal via ⅛" osteotome and burr to allow for valgus positioning of the knee;
    d. Complete the removal (to the rim) of the posterior and posterior-lateral meniscus; and
    e. Confirm sizing of the prosthesis by measuring distance from resected meniscus to remaining anterior meniscus.
4. Medial parapatellar arthrotomy (mid-patella to tibial joint line).
5. Complete removal of visible osteophytes along the medial femoral condyle.
6. Insert thickness gauge and size for thickness of prosthesis.
7. Insert trial component:
    a. Flex knee to approximately 50+ degrees to fully expose the distal portion of the femoral condyle;
    b. Insert trial component; and
    c. While applying insertion pressure, apply valgus stress to the tibia and "stretch-extend" the tibia over the trial component.
8. Check for proper sizing with "true lateral" and anterior/posterior fluoroscope images of the knee while in extension:
    a. Ideally, the prosthesis should be within 1 mm of the anterior/posterior boundaries of the tibial plateau and superimposed over the medial boundary.
9. Remove trial component and flush joint with saline.
10. Insert the appropriate prosthesis.
11. Confirm proper placement and sizing with fluoroscopic images as with trial component.
12. Maintain leg in extension and close wound after insertion of a Hemovac drain.
13. Place leg in immobilizer prior to patient transfer.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed is:

1. A unicompartmental knee prosthesis for implantation into a knee joint compartment between a femoral condyle and its corresponding tibial plateau, the prosthesis comprising:

a body having a generally elliptical shape in plan, the body including a pair of opposed surfaces and a peripheral edge extending between the pair of opposed surfaces and having a first side, a second side opposite the first side, a first end, and a second end opposite the first end, the prosthesis configured to be translatable with respect to the tibial plateau during knee articulation, the body including at least one cusp protruding downwardly from one of the first and second ends for limiting translation of the prosthesis, the body having an exterior portion and an interior portion, wherein the exterior portion encapsulates the interior portion and the exterior portion is constructed from a higher modulus material than the interior portion.

2. The prosthesis according to claim 1, wherein the interior portion is substantially hollow.

3. The prosthesis according to claim 1, wherein the interior portion is constructed from a material selected from the group consisting of hydrogels, elastomeric polymers, and viscouselastic materials.

4. The prosthesis according to claim 1, wherein the exterior portion is constructed of a biocompatible material selected from the group consisting of ceramics, metals, metal alloys, hydrogels, thermoset or thermoplastic polymers, or composites thereof.

5. The prosthesis according to claim 1, wherein at least one of the exterior portion and the interior portion is constructed at least partially of a material capable of containing living cells.

6. The prosthesis according to claim 1, further comprising a surface coating applied to the exterior portion.

7. The prosthesis according to claim 1, wherein at least one of the exterior portion and interior portion includes an active material associated therewith.

8. The prosthesis according to claim 1, further including a locking mechanism disposed in the interior portion and arranged to connect the pair of opposed surfaces.

9. The prosthesis according to claim 8, wherein the locking mechanism includes a first mating component affixed to a first one of the pair of opposed surfaces and a second mating component affixed to a second one of the pair of opposed surfaces and arranged to be securely received by the first mating component, wherein the first and second mating components can move relative to one another.

10. The prosthesis according to claim 1, wherein the pair of opposed surfaces includes a top surface that is generally concave.

11. The prosthesis according to claim 1, wherein the pair of opposed surfaces includes a bottom surface that is generally flat.

12. The prosthesis according to claim 1, wherein the pair of opposed surfaces are contoured such that the prosthesis is self-centering within the knee joint compartment.

13. The prosthesis according to claim 1, wherein a first dimension D is defined by the first end and the second end, and a second dimension F is defined by the first side and the second side, wherein the dimension F is from about 0.25D to about 1.5D.

14. The prosthesis according to claim 1, wherein a section across the body from the first side to the second side has a thickness at a periphery of the first side which is larger on average than a thickness at a periphery of the second side.

15. The prosthesis according to claim 1, wherein a periphery of the body is on average of greater thickness than a central portion of the body.

16. A method for implantation of a unicompartmental knee prosthesis into a knee joint compartment between a femoral condyle and its corresponding tibial plateau, the method comprising:

providing a prosthesis including a body having a generally elliptical shape in plan, the body including a pair of opposed surfaces and a peripheral edge extending between the pair of opposed surfaces and having a first side, a second side opposite the first side, a first end, and a second end opposite the first end, the prosthesis configured to be translatable with respect to the tibial plateau during knee articulation, the body including at least one cusp protruding downwardly from one of the first and second ends for limiting translation of the prosthesis, the body having an exterior portion and an interior portion, wherein the exterior portion encapsulates the interior portion and the exterior portion is constructed from a higher modulus material than the interior portion;

surgically exposing the knee joint compartment; and inserting the prosthesis into the knee joint compartment.

17. The method according to claim 16, further comprising providing an active material associated with the body.

18. The method according to claim 16, further comprising determining a size and shape of the prosthesis required by examination of the knee joint using one or more of X-ray imaging and MRI imaging.

19. The method according to claim 16, further comprising selecting the prosthesis from a library of prostheses of standard shapes and sizes.

20. The method according to claim 16, further comprising generating a custom prosthesis whose size and shape are at least partially based on an examination of the knee joint.

21. The method according to claim 16, further comprising pre-loading the prosthesis during implantation.

22. A method for correcting misalignment in an axis of rotation of a knee joint, the method comprising:

providing a unicompartmental knee prosthesis including a body having a generally elliptical shape in plan, the body including a pair of opposed surfaces and a peripheral edge extending between the pair of opposed surfaces and having a first side, a second side opposite the first side, a first end, and a second end opposite the first end, the prosthesis configured to be translatable with respect to the tibial plateau during knee articulation, the body including at least one cusp protruding downwardly from one of the first and second ends for limiting translation of the prosthesis, the body having an exterior portion and an interior portion, wherein the exterior portion encapsulates the interior portion and the exterior portion is constructed from a higher modulus material than the interior portion;

surgically exposing the knee joint; and inserting the prosthesis into the knee joint to at least partially correct the misalignment of the axis of rotation.

23. The method according to claim 22, wherein inserting the prosthesis includes inserting the prosthesis into a medial compartment of the knee joint and moving the axis to a less varus condition.

24. The method according to claim 22, wherein inserting the prosthesis includes inserting the prosthesis into a lateral compartment of the knee joint and moving the axis of rotation to a less valgus condition.

* * * * *